United States Patent [19]

Reller et al.

[11] 4,276,430

[45] Jun. 30, 1981

[54] ANALGESIC AND ANTI-INFLAMMATORY COMPOUNDS AND COMPOSITIONS CONTAINING SAME

[75] Inventors: Herbert H. Reller; Herbert C. Kretschmar, both of Cincinnati, Ohio

[73] Assignee: The Procter & Gamble Company, Cincinnati, Ohio

[21] Appl. No.: 61,107

[22] Filed: Jul. 26, 1979

Related U.S. Application Data

[63] Continuation-in-part of Ser. No. 855,042, Nov. 25, 1977, abandoned, which is a continuation-in-part of Ser. No. 750,981, Dec. 15, 1976.

[51] Int. Cl.$^3$ .................. C07C 69/86; C07C 69/88
[52] U.S. Cl. ................................ 560/66; 560/252; 560/254; 560/255; 424/308
[58] Field of Search ................ 560/64, 66, 252, 254, 560/255; 424/308

[56] References Cited

FOREIGN PATENT DOCUMENTS 1220447  1/1971  United Kingdom .................. 560/66
1393326  5/1975  United Kingdom .................. 560/66

OTHER PUBLICATIONS

Chemical Abstracts 86:72221w vol. 86, 1977.
Chemical Abstracts 89:108720m vol. 89, 1978.
Chemical Abstracts 83:78903e vol. 83, 1975.

*Primary Examiner*—Paul J. Killos
*Attorney, Agent, or Firm*—Donald E. Hasse; Michael J. Roth; Richard C. Witte

[57] ABSTRACT

Dihydroxybenzoic acid derivatives and compositions containing same are useful for topical application to the skin as well as for systemic administration. The compounds are especially effective for providing an analgesic, anti-pyretic, and anti-inflammatory effect.

39 Claims, No Drawings

ANALGESIC AND ANTI-INFLAMMATORY COMPOUNDS AND COMPOSITIONS CONTAINING SAME

REFERENCE TO RELATED APPLICATIONS

This application is a continuation-in-part of United States application Ser. No. 855,042 filed Nov. 25, 1977, now abandoned which in turn is a continuation-in-part of United States application Ser. No. 750,981, filed Dec. 15, 1976.

BACKGROUND OF THE INVENTION

This invention relates to dihydroxybenzoic acid derivatives. More particularly, the invention relates to 2,5-dihydroxybenzoic acid derivatives, compositions containing same, and the topical and systemic, especially oral, use thereof with animals, including humans, to provide an analgesic and anti-inflammatory effect.

Tissue inflammation is the result of interconnected physiological events. Inflammation of the skin which is associated with tissue damage can result from various skin disorders such as eczema, psoriasis, seborrheic dermatitis, contact dermatitis, allergic dermatitis, etc. Inflammation is also associated with tissue damage resulting from ultraviolet or thermal burns, attack by certain microorganisms, insect bites, stings, etc. Inflammation of deeper structures, the muscles, tendons, bursa and joints, which is associated with tissue damage, can result from physical trauma, e.g., sprains, strains, contusions, strenuous exercise, etc. Such inflammation may result in bursitis, tendinitis, and muscle soreness. Inflammation and pain are also associated with tissue damage resulting from metabolic disorders, such as gout, or from immunologic disorders, such as rheumatoid arthritis, or from changes associated with aging, such as osteoarthritis.

Symptoms of inflammation are erythema (redness), edema (swelling), heat, pain, and loss of function. The immediate consequence of tissue damage is the release of certain chemical agents which are mediators of inflammation, i.e. these materials evoke and intensify the events which result in the redness, swelling, pain and heat. Examples of these chemical agents are histamine, serotonin and the kinins.

Among the important mediators of inflammation are certain prostaglandins. In contrast to histamine, serotonin and the kinins, the prostaglandins are continuously biosynthesized and released from cells at the inflammatory site. Thus, the prostaglandins have a longer lasting effect. Various anti-inflammatory compounds are known inhibitors of prostaglandin synthesis. One commonly used anti-inflammatory/analgesic drug is aspirin. Aspirin, of course, is a well known oral drug. However, when administered orally, aspirin is known to cause gastric irritation and frank stomach bleeding in up to 70% of patients using aspirin-based products. Recent studies have also indicated aspirin can delay and decrease inflammation in humans when applied topically. However, it has been found that a relatively high concentration of aspirin must be topically applied before its effect as a topical analgesic is noted. Unfortunately, the repeated topical application of a high level of aspirin causes primary irritation and peeling of the superificial layers (the stratum corneum) of the skin.

Accordingly, there is a continuing need for analgesic/antiinflammatory agents which can be used orally or topically without adverse secondary effects.

It is an object of this invention to provide compounds which are useful as analgesic and anti-inflammatory agents.

It is another object of this invention to provide compounds which can be systemically and topically administered to provide an analgesic effect and to alleviate inflammation.

SUMMARY OF THE INVENTION

The present invention is based on the discovery that derivatives of 2,5-dihydroxybenzoic acid exhibit superior analgesic and antiinflammatory properties without the negative side effects associated with many salicylate compounds, e.g., aspirin. The compounds encompassed by this invention are of the formula

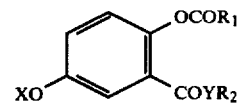

wherein $R_1$ is an alkyl group having from 1 to 4 carbon atoms, Y is O, NH or $NR_2$, $R_2$ is a saturated or unsaturated aliphatic group having from 1 to 14 carbon atoms, benzyl or phenyl and X is H or $COR_3$ where $R_3$ is an alkyl group having from 1 to 4 carbon atoms provided $R_2$ has at least 2 carbon atoms when Y is O, X is $COR_3$, and $R_1$ and $R_3$ are $CH_3$.

The 2,5-dihydroxybenzoic acid derivatives (including those wherein $R_2$ contains 1 carbon atom when Y is O, X is $COR_3$, and $R_1$ and $R_3$ are $CH_3$) described herein can be formulated with a pharmaceutically acceptable carrier for topical application to skin, or can be administered systemically, all as described more fully hereinafter.

DETAILED DISCUSSION

Novel dihydroxybenzoic acid derivatives useful herein for providing analgesic effects have the following formula

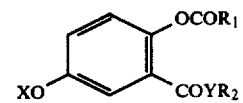

wherein $R_1$ is an alkyl group having from 1 to 4 carbon atoms, Y is O, NH or $NR_2$, $R_2$ is a saturated or unsaturated aliphatic group having from 1 to 14 carbon atoms, benzyl or phenyl and X is H or $COR_3$ where $R_3$ is an alkyl group having from 1 to 4 carbon atoms, provided $R_2$ has at least 2 carbon atoms when Y is O, X is $COR_3$, and $R_1$ and $R_3$ are $CH_3$. The saturated or unsaturated aliphatic group includes alkyl, alkenyl, alkadienyl, alkatrienyl, alkynyl and alkadiynyl groups.

As used herein the saturated or unsaturated aliphatic, benzyl or phenyl groups represented by $R_2$ can be substituted with acetoxy; alkyloxy, e.g. methoxy, ethoxy and butoxy; alkylamido, e.g. methylamido, ethylamido and butylamido; halogen, e.g. chloro, bromo and fluoro; amino; nitro; alkyl, e.g. methyl, propyl and butyl; amido; and hydroxy moieties without adversely affecting the efficacy of the dihydroxybenzoic acid derivatives above defined. Such moieties can be in the ortho, meta or para positions when $R_2$ is benzyl or phenyl.

In general, the compounds herein are prepared from a dihydroxybenzoic acid. One hydroxy moiety is in the 2-position while the second hydroxy moiety is in the 5-position. The dihydroxybenzoic acid is initially acylated with an appropriate anhydride of the formula $(RCO)_2O$ wherein R has from 1 to 4 carbon atoms. Examples of the anhydride are acetic anhydride, propionic anhydride, butyric anhydride, valeric anhydride and pivalyl anhydride. If X is to be $COR_3$, two moles of the appropriate anhydride are reacted with each mole of the dihydroxybenzoic acid. The reaction proceeds in the presence of sulfuric acid at a temperature from 40° C. to 80° C. The resultant diacyloxy benzoic acid is next reacted to form an ester or an amide thereof. The ester is formed by reacting the diacyloxy benzoic acid with oxalyl chloride or sulfonyl chloride to provide a diacyloxy benzoyl chloride. This compound is then reacted with an alcohol in the presence of pyridine to provide the desired ester. Suitable alcohols include ethanol, propanol, sec-propanol and primary, secondary and tertiary, -butanol, -hexanol, -decanol, and -dodecanol; unsaturated alcohols, e.g. allyl alcohol, crotyl alcohol, 3-hexenol, 2-hexenol, 2-octenol, 3-dodecenol, 2,4-hexadienol 3,5-octadien-2-ol, 9,11-dodecadien-3-ol, 4,6-heptadien-2-ol; benzyl alcohol; and phenol.

The amide compounds of the present invention, i.e. when Y is NH or $NR_2$, are provided by reacting the acyloxy benzoyl chloride with a suitable amine. This reaction occurs at a temperature of 0° C. to 30° C.

Dihydroxybenzoic acid derivatives described herein where X is hydrogen are prepared from the known 2-acetoxy-5-hydroxybenzoic acid [see M. Bergmann and P. Dangshot, Berichte, 52, 371 (1919)]. Other acyloxy substituted hydroxybenzoic acid starting materials are prepared using the general procedure outlined by Bergmann and Dangshot. The hydroxy moiety is protected by treatment with trimethylsilyl chloride. The protected acid is then converted to the ester or amide by sequential reaction with oxalyl chloride and an alcohol or amine as described above where X is $COR_3$. The desired compound is obtained by removal of the trimethylsilyl moiety with tetrabutylammonium fluoride in tetrahydrofuran.

Preferred dihydroxybenzoic acid derivatives are those wherein Y is O and X is $COR_3$. More preferred dihydroxybenzoic acid derivatives are those wherein Y is O, X is $COR_3$, $R_2$ is an alkyl group having from 6 to 8 carbon atoms or benzyl, and $R_1$ and $R_3$ are methyl or tertiary butyl. Highly preferred compounds are benzyl 2,5-diacetoxybenzoate and hexyl 2,5-diacetoxybenzoate.

The following compounds are exemplary dihydroxybenzoic acid derivatives:
Isopropyl 2,5-diacetoxybenzoate
Propyl 2,5-diacetoxybenzoate
Hexyl 2,5-diacetoxybenzoate
2'-ethylhexyl 2,5-diacetoxybenzoate
Decyl 2,5-diacetoxybenzoate
Dodecyl 2,5-diacetoxybenzoate
Methyl 2,5-dipropionoxybenzoate
Octyl 2,5-dipropionoxybenzoate
Hexyl 2,5-dipivaloxybenzoate
Decyl 2,5-dibutyroxybenzoate
Butyl 2-acetoxy-5-hydroxybenzoate
Hexyl 2-propionoxy-5-hydroxybenzoate
3',5'-Hexadienyl 2,5-diacetoxybenzoate
2'-Hexenyl 2,5-diacetoxybenzoate
9',11'-Dodecadienyl 2,5-diacetoxybenzoate
Benzyl 2,5-dibutyroxybenzoate
Benzyl 2,5-diacetoxybenzoate
Benzyl 2,5-dipivaloxybenzoate
Benzyl 2-acetoxy-5-hydroxybenzoate
Phenyl 2,5-diacetoxybenzoate
Phenyl 2-acetoxy-5-hydroxybenzoate
2,5-Diacetoxy-N-hexylbenzamide
2,5-Dipropionoxy-N-octylbenzamide
2,5-Diacetoxy-N-dibutylbenzamide
p-Acetamidophenyl 2,5-diacetoxybenzoate
5'-Hydroxyhexyl 2,5-diacetoxybenzoate
6'-Acetoxyhexyl 2,5-diacetoxybenzoate
6'-Fluorohexyl 2,5-diacetoxybenzoate
6'-Nitrohexyl 2,5-diacetoxybenzoate
6'-Methylamidohexyl 2,5-diacetoxybenzoate
2'-Ethyl-2',4'-hexadienyl 2,5-diacetoxybenzoate
2'-Acetoxybenzyl 2,5-dipropionoxybenzoate
2'-Fluorobenzyl 2,5-diacetoxybenzoate
2'-Hydroxybenzyl 2,5-diacetoxybenzoate
2'-Methoxybenzyl 2,5-diacetoxybenzoate
2',4'-Diacetoxybenzyl 2,5-diacetoxybenzoate
2'-Acetamidobenzyl 2,5-diacetoxybenzoate The following examples illustrate the preparation of the dihydroxybenzoic acid derivatives of the foregoing type but are not intended to be limiting of the method of preparation. Example I describes a very convenient "one-pot" synthesis of the most highly preferred compound herein, benzyl 2,5-diacetoxybenzoate.

EXAMPLE I

Esterification and Acylation of 2,5-dihydroxybenzoic acid

A five liter three-neck flask fitted with a water-cooled Friedrich's condenser, a 500 ml addition funnel, a thermometer, a teflon covered magnetic stirring bar, and a heating mantle is charged with 400 grams of 2,5-dihydroxybenzoic acid and 1200 ml of acetonitrile. The solution is heated to 40° C., and 360 ml of triethylamine is added in a slow stream (ca. 10 min.). The addition of triethylamine increases the temperature of the mixture to ca. 65° C. The addition funnel is rinsed with 200 ml of acetonitrile which is then added to the reaction mixture. To this reaction mixture is added 316 ml of benzyl bromide in a slow stream (ca. 10 min.). The addition funnel is washed with 200 ml of acetonitrile which is then added to the reaction mixture. The reaction mixture is heated to ca. 80° C., and stirred at that temperature for 24 hours.

The heating element is turned off and 522 ml of pyridine is run into the flask (pot temperature ca. 70° C.). To this mixture, 516 ml of acetic anhydride is added dropwise (ca. 15 min.). The mixture is again heated to reflux ca. 80° C., and maintained at that temperature for 20 hours.

The flask is cooled, the solution is divided into three approximately equal portions and the acetonitrile is removed on a rotary evaporator. Each portion is then transferred to a separatory funnel with three liters of ethyl ether where it is sequentially washed twice with 750 ml of 1 N HCl, once with 1 liter of $H_2O$, once with 500 ml of saturated aqueous sodium bicarbonate, once with 1 liter of water, and once with 500 ml of brine. The ether solution is dried with anhydrous $MgSO_4$. The drying agent is filtered and the ether evaporated to recover the product. The crude product is recrystallized from ethanol, filtered, and dried in a vacuum desiccator. Benzyl 2,5-diacetoxybenzoic acid has a melting point of 71°–73° C. and is obtained in approximately 80% yield.

EXAMPLE II

Benzyl 2,5-diacetoxybenzoate

A solution of gentisic acid (874 gr., 5.7 moles), freshly distilled acetic anhydride (2315 gr., 22.7 moles) and concentrated sulfuric acid (2 ml) is heated at 80° C. for 45 minutes and stirred at ambient temperatures for 72 hours. Approximately 1200 ml of acetic anhydride is removed by distillation at 70° C. and 30 mm pressure. The residue is poured into 7.5 liters of water. After being stirred for 2 hours, the colorless precipitate is collected by suction filtration, washed with an additional 2 liters of water, and dried under vacuum for 16 hours (80° C. and 1 mm pressure). The precipitate is slurried with 2 liters of hexane, collected by suction filtration, and dried under vacuum for 16 hours (80° C. and 1 mm pressure). The precipitate is again stirred with 1800 ml water and allowed to settle. The purification process is repeated two times and then the precipitate is collected by suction filtration and dried under vacuum for 64 hours (80° C. and 1 mm pressure). The dried colorless crystals weigh 1052 grams (78% yield), have a m.p. of 121.5° C.–125° C., and are identified as 2,5-diacetoxybenzoic acid.

To the diacetoxybenzoic acid (225.2 gr., 0.95 moles) are added oxalyl chloride (1800 gr., 14.18 moles) and dry chloroform (250 ml). The oxalyl chloride and dry chloroform are initially cooled to 0° C. prior to addition to the diacetoxybenzoic acid. The resultant mixture is stirred under an argon atmosphere for 48 hours. The excess oxalyl chloride is removed by distillation under vacuum (45° C. and 30 mm pressure). The colorless residue is washed with 2100 ml of hexane and dried under vacuum (45° C. and 0.1 mm pressure). The resultant product is identified as 2,5-diacetoxybenzoyl chloride and has a m.p. of 89° C.–94.5° C.

To a solution of the 2,5-diacetoxybenzoyl chloride (250.7 gr., 0.98 moles) in 750 ml of dry chloroform at 0° C. is added a solution of benzyl alcohol (100.63 gr., 0.93 moles) and pyridine (140 gr., 1.77 moles) in 150 ml f dry chloroform. The addition is made dropwise over a six hour period. The temperature is maintained at 0° C.–5° C. during the addition and the entire operation is performed under an argon atmosphere. The reaction mixture is stirred at 26° C. for 16 hours and poured into 300 ml cold water. The organic portion is extracted with 3.4 liters of ether and is washed with 200 ml of 15% hydrochloric acid, 1200 ml water, 500 ml sodium hydroxide (0.1 N), 2400 ml water, and dried over magnesium sulfate. Evaporation of the solvents gives 292.6 grams (89% yield) of light pink crystals. The crystals are recrystalized twice from methanol to yield 132 grams (40% yield) of colorless crystals having a m.p. of 71° C.–73° C. and identified as benzyl 2,5-diacetoxybenzoate.

The nmr (CDCl$_3$) shows signals at: $\tau$2.25 (S, J=2 Hz) [1.2] C-6 aromatic proton, $\tau$2.6 (s) [4.8] aromatic protons of benzyl ester, $\tau$2.6–3.0 (m) [2.3] C-3 and C-4 aromatic protons, $\tau$4.7(s) [2.3] benzyl protons, $\tau$7.7(s) [2.8] acetate methyl group, $\tau$7.85(s) [2.8] acetate methyl group. Analysis calculated for C$_{18}$H$_{16}$O$_6$: C, 65.85; H, 4.9. Found C, 65.83; H, 5.05.

EXAMPLE III

Hexyl 2,5-diacetoxybenzoate

A solution of 2,5-diacetoxybenzoyl chloride (60 gr., 0.234 mole) in 240 ml of dry chloroform is added dropwise over a six hour period to a solution of hexyl alcohol (21.7 gr., 0.202 mole) and pyridine (33.61 gr., 0.425 mole) in 100 ml of chloroform. The temperature is maintained at 0° C.–5° C. during the addition and the entire operation is performed under an argon atmosphere. The reaction mixture is stirred for 16 hours at 26° C. and is diluted with 800 ml of ether. The organic layer is washed sequentially with 280 ml of 1 N hydrochloric acid, 3×100 ml water, 125 ml of 1 N sodium hydrochloride, 3×100 ml water and dried over magnesium sulfate. Evaporation of the solvents affords 68.1 grams (99%) of light yellow liquid. Distillation in a short-path still affords 46.2 grams (68%) of hexyl 2,5-diacetoxybenzoate as a colorless liquid having a b.p. of 165° C./0.3 mm.

The nmr (CDCl$_3$) shows signals at: $\tau$2.38 (d, J=2 Hz) [0.92] C-6 aromatic proton, $\tau$2.7–3.17 (m) [2.11] C-3 and C-4 aromatic protons, $\tau$5.8 (t, J=6 Hz) [1.83] methylene protons $\alpha$ to oxygen, $\tau$7.72 (s) and $\tau$7.77 (s) [6.24] the two acetate methyl groups, $\tau$8.1–9.15 (m) [11.01] remaining protons.

EXAMPLE IV

Benzyl 2,5-dipropionoxybenzoate

A solution of gentisic acid (10 gr., 0.065 mole), freshly distilled propionic anhydride (33.8 gr., 0.26 mole) and 3 drops of concentrated sulfuric acid is heated at 60° C. for 25 minutes, stirred at ambient temperature for 16 hours and then poured into 900 ml of water. After being stirred for two hours, the colorless precipitate is collected by suction filtration, washed with 3×300 ml of water and dried under vacuum for 16 hours (80° C./1 mm pressure). The precipitate is slurried with two liters of hexane, collected by suction filtration and dried under vacuum for 16 hours (60° C./1 mm pressure). The dried colorless crystals weigh 26.4 grams (88% yield), have a m.p. of 132° C.–134° C. and are identified as 2,5-dipropionoxybenzoic acid.

Oxalyl chloride (100 gr., 0.79 mole) and the 2,5-dipropionoxybenzoic acid (10 gr., 0.038 mole) are combined and this mixture is stirred under an argon atmosphere for 48 hours. The excess oxalyl chloride is removed by distillation under vacuum (45° C./30 mm pressure). The colorless residue is washed with 2×10 ml hexane and stripped under vacuum (45° C./0.1 mm pressure). This process affords 10.33 grams of colorless liquid identified as 2,5-dipropionoxybenzoyl chloride. This material is used without further purification.

To a solution of 2,5-dipropionoxybenzoyl chloride (10.3 gr., 0.036 mole) in 30 ml dry chloroform at 0° C. is added dropwise over a six hour period a solution of benzyl alcohol (3.45 gr., 0.032 mole) and pyridine (5.05 gr., 0.064 mole) in 6 ml of dry chloroform. The temperature is maintained at 0° C.–5° C. during the addition and the entire operation is performed under an argon atmosphere. The reaction is stirred at 26° C. for 16 hours and poured into 50 ml of cold water. The organic portion is extracted with 450 ml of ether and the organic layer is washed with 80 ml of 15% HCL (hydrochloric acid), 3×100 ml water, 100 ml of 1 N sodium hydroxide, 3×100 ml water, and dried over magnesium sulfate. Evaporation of the solvents affords 10.22 grams (90%)

of benzyl 2,5-dipropionoxybenzoate as a colorless liquid. Distillation in a Hickman still affords 7.0 grams (60%) of benzyl 2,5-dipropionoxybenzoate as a colorless liquid of b.p. 227° C./0.14 mm.

The nmr (CDCl$_3$) shows signals at: $\tau$2.37 (d, J=2 Hz) [0.84] C-6 aromatic proton, $\tau$2.55–3.1 (m) [7.18] C-3, C-4 and aromatic ester protons, $\tau$4.72 (s) [1.86] benzyl protons, $\tau$7.17–7.99 (overlapping Q) [3.88] methylene protons α to the propionyl carbonyl, $\tau$8.57–9.1 (overlapping, t) [6.25] methyl protons.

EXAMPLE V

Benzyl 2,5-dipivaloxybenzoate

A solution of gentisic acid (10.34 gr., 0.067 mole), freshly distilled pivalyl anhydride (50 gr., 0.27 mole) and six drops of concentrated sulfuric acid is heated at 60° C. for one hour and stirred at ambient temperature for two hours. The reaction mixture is poured into 900 ml of water and stirred for two hours. The liquid that precipitates is extracted with 800 ml of ether. The ethereal layer is washed with 4×50 ml warm water and dried over magnesium sulfate. Evaporation of the ether affords 47 grams of waxy solid. This solid is triturated with 10×100 ml water, collected by suction filtration and washed with an additional 300 ml of water. Air drying is followed by drying in a vacuum oven (60° C./1 mm pressure) for 16 hours to give 12.04 grams (56%) of 2,5-dipivaloxybenzoic acid as colorless crystals with a m.p. of 159° C.-162° C.

Oxalyl chloride (100 gr., 0.793 mole) and 2,5-dipivaloxybenzoic acid (10 gr., 0.031 mole) are combined and stirred at 26° C. under an argon atmosphere for 18 hours. The excess oxalyl chloride is removed by stripping (35° C./1 mm pressure) for four hours. The colorless liquid obtained in this manner is used without further purification.

To a solution of the 2,5-dipivaloxybenzoyl chloride (10.65 gr., 0.031 mole) in 30 ml of dry chloroform at 0° C. is added dropwise over a two hour period a solution of benzyl alcohol (2.88 gr., 0.027 mole) and pyridine (4.22 gr., 0.053 mole) in 6 ml of dry chloroform. The temperature is maintained at 0° C.-5° C. during the addition and the entire operation is performed under an argon atmosphere. The reaction is stirred at 26° C. for 16 hours and poured into 50 ml of cold water. The organic portion is extracted with 450 ml of ether and is washed with 80 ml of 15% HCL, 3×50 ml water, 25 ml sodium hydroxide (0.1 N), 4×50 ml water and dried over magnesium sulfate. Evaporation of the solvents affords 11.61 grams of colorless crystals. These crystals are recrystallized from 40 ml hexane to yield 6.5 grams (59%) of benzyl 2,5-dipivaloxybenzoate as colorless crystals having a m.p. of 90.5° C.-91.8° C.

The nmr (CDCl$_3$) shows signals at: $\tau$2.37 (d, J=3 Hz) [1.08] C-6 aromatic proton, $\tau$2.53–3.13 (m) [7.56] C-3, C-4, and aromatic ester protons, $\tau$4.7 (s) [2.16] benzyl protons, $\tau$8.63 (s) [17.29] methyl protons.

EXAMPLE VI 2,5-diacetoxy-N-hexylbenzamide

To a solution of 2,5-diacetoxybenzoyl chloride (2.56 gr., 0.01 mole) in 10 ml dry chloroform at 0° C. is added dropwise over a one hour period a solution of n-hexylamine (2.12 gr., 0.021 mole) in 10 ml of dry chloroform. The temperature is maintained at 0° C.-5° C. during the addition and the entire operation is performed under an argon atmosphere. After the addition is complete, the solution is stirred at 26° C. for 16 hours. The organic portion is extracted with 80 ml chloroform and is washed with 30 ml of 0.1 N HCl, 20 ml water, 10 ml sodium hydroxide (0.25 N), 20 ml water and dried over magnesium sulfate. Evaporation of the solvents affords 3.57 grams of pink crystals. These crystals are recrystallized from 550 ml of hexane to yield 1.8 grams (56%) of 2,5-diacetoxy-N-hexylbenzamide as colorless crystals, m.p. 76.5° C.-77° C.

The nmr (CDCl$_3$) shows signals at: $\tau$2.55 (d, J=3 Hz) [0.86] C-6 aromatic proton, $\tau$2.7–3.1 (m) [2.11] C-3 and C-4 aromatic protons, $\tau$3.7 (broad s) amide proton, $\tau$6.4–6.9 (m) [2.04] methylene protons α to nitrogen, $\tau$7.7 (s) [5.76] acetate methyl groups, $\tau$8.6–9.1 (m) [12.2] remaining protons.

EXAMPLE VII p-Acetamidophenyl 2,5-diacetoxybenzoate

A solution of 2,5-diacetoxybenzoyl chloride (95 gr., 0.37 mole) in 320 ml of dry chloroform is added dropwise over a 4 hour period to a solution of 4-acetamidophenol (50.85 gr., 0.34 mole) and pyridine (98.3 gr., 1.24 moles). The temperature is maintained at 0° C.-5° C. during the addition and the entire operation is performed under an argon atmosphere. After the addition, the reaction mixture is stirred at 26° C. for 16 hours. The organic portion is extracted with 1.0 liter of ether and is washed with 950 ml of 15% HCL, 3×300 ml water, 150 ml sodium hydroxide (1 N), 3×10 ml water and dried over magnesium sulfate. Evaporation of the solvents afford 141.7 grams of colorless semi-solid material. Recrystallization from 1.5 liters of benzene affords 59.24 grams (47%) of p-acetamidophenyl 2,5-diacetoxybenzoate as colorless crystals of m.p. 148° C.-149.5° C.

The nmr (CDCl$_3$) spectrum shows signals at: $\tau$1.82–3.13 (m) [8.03] C-6, C-3, C-4 aromatic protons, aromatic phenyl ester protons and the amide proton, $\tau$7.7 (2 overlapping, s) [5.84] acetate methyl groups, $\tau$7.87 (s) [3.16] acetamido methyl group.

EXAMPLE VIII 2,4-Hexadienyl-2,5-diacetoxybenzoate

To a solution of 2,5-diacetoxybenzoyl chloride (1.6 gr., 0.0064 mole) in 8 ml of dry chloroform at 0° C. is added dropwise over a one hour period a solution of 2,4-hexadienol (0.6 gr., 0.006 mole) and pyridine (0.925 gr., 0.012 mole) in 8 ml of dry chloroform. The temperature is maintained at 0° C.-5° C. during the addition and the entire operation is performed under an argon atmosphere. The reaction is stirred at 26° C. for 16 hours and poured into 35 ml of cold water. The organic portion is extracted with 80 ml of chloroform and is washed with 70 ml of 0.1 N HCL, 35 ml water, 10 ml sodium hydroxide (0.1 N), 35 ml water and dried over magnesium sulfate. Evaporation of the solvents affords 1.6 grams of soft crystals. These crystals are recrystallized from hexane to give 0.91 grams (49%) of soft colorless crystals identified as the subject compound.

The nmr (CDCl$_3$) shows signals at: $\tau$2.3 (d, J=2 Hz) C-6 aromatic protons, $\tau$2.58–31 (m) [2.5] C-3 and C-4 aromatic protons, $\tau$3.4–4.77 (broad m) [2.95] olefinic protons, $\tau$5.3 (d, J=7 Hz) [1.34] methylene protons α to oxygen, $\tau$7.7 and 7.73 (two s) [7.15] acetate methyl groups, $\tau$8.28 (d, J=6 Hz) [2.55] methyl group.

EXAMPLE IX n-Butyl 2,5-diacetoxybenzoate

To a solution of 2,5-diacetoxybenzoyl chloride (2.0 gr., 0.008 mole) in 15 ml of dry chloroform is added dropwise over a 30 minute period a solution of n-butanol (2.567 gr., 0.008 mole) and pyridine (0.80 gr., 0.011 mole) in 25 ml of dry chloroform. The entire operation is performed at room temperature and under an argon atmosphere. The reaction is stirred at 26° C. for 16 hours. The chloroform is removed on a rotary evaporator and the residue taken up in 60 ml of ether, transferred to a separatory funnel and washed once with 25 ml water, 3×25 ml hydrochloric acid (1 N), 3×25 ml saturated aqueous sodium bicarbonate, 2×25 ml water and 25 ml brine. The remaining ether solution is dried over magnesium sulfate, filtered and evaporated to a light tan oil. The crude product is purified by bulb-to-bulb distillation in a Kugelrohr oven yielding 1.48 grams (60%) of colorless oil identified as the n-butyl 2,5-diacetoxybenzoate.

The nmr (CDCl$_3$) shows signals at $\tau$2.27 (d, J=2 Hz, 1H, aromatic), 2.6–3.1 (m, 2H, C$_3$ and C$_4$ aromatic), 5.75 ($\tau$, J=6 Hz, 2H, oxymethylene), 7.68 and 7.75 (s, 3 each, acetate methyl), 8.0–8.9 (m, 4H, methylene), 9.06 (m, 3H, butyl methyl).

EXAMPLE X

Benzyl 2-acetoxy-5-hydroxybenzoate

A flask is fitted with a stirring bar and charged with 5.0 grams (0.0255 mole) of 2-acetoxy-5-hydroxybenzoic acid [M. Bergmann and P. Dangschat, Berichte, 52, 371 (1919)]. After the flask is flushed with argon and cooled in an ice bath, a solution of t-butyldimethylsilylchloride (9.23 gr., 0.06122 mole) and imidazole (8.5 gr., 0.125 mole) dissolved in 20 ml of anhydrous dimethylformaldehyde (DMF) is added dropwise over a 30 minute period. The reaction mixture is stirred at room temperature overnight. The DMF is removed in vacuo. The residue is taken up in ether (75 ml) transferred to a separatory funnel and extracted with 1 N HCl (3×25 ml), 5% NaOH (3×25 ml), water (2×10 ml) and brine (20 ml). The ether extract is dried over sodium sulfate, filtered and the solvents removed in vacuo to yield 2-acetoxy-5-t-butyldimethylsilylbenzoic acid.

To a solution of the 2-acetoxy-5-t-butyldimethylsilylbenzoic acid in chloroform (20 ml) cooled in an ice bath is added dropwise oxalyl chloride (23.3 gr., 0.183 mole over a 1 hour period. The solution is allowed to stir overnight at room temperature. The excess oxalyl chloride is removed on a rotary evaporator and the resulting product is immediately dissolved in chloroform (25 ml), blanketed with argon and cooled in an ice bath. To this solution is added dropwise a solution of benzyl alcohol, pyridine, and chloroform over a 1 hour period. The reaction is stirred at room temperature for 4 hours. The chloroform is removed on a rotary evaporator, the residue dissolved in ether, and transferred to a separatory funnel. The ether layer is then extracted with 1 N HCl, 5% sodium hydroxide, water and brine. The ether is dried over magnesium sulfate, filtered and evaporated to yield benzyl 2-acetoxy-5-t-butyldimethylsilylbenzoate. The above ester is dissolved in tetrahydrofuran and a solution of tetrabutylammonium fluoride and tetrahydrofuran is added.

The above ester is dissolved in tetrahydrofuran and a solution of tetrabutylammonium fluoride and tetrahydrofuran is added at room temperature. The reaction mixture is stirred at room temperature. The tetrahydrofuran is removed on a rotary evaporator, the residue taken up in ether, transferred to a separatory funnel and extracted with water and brine. The remaining ether solution is dried over magnesium sulfate, filtered and evaporated to yield benzyl 2-acetoxy-5-hydroxybenzoate.

Topical Compositions

The dihydroxybenzoic acid derivatives as described above are useful when topically applied to skin. Compositions containing the dihydroxybenozic acid derivatives where R$_2$ contains 1 carbon atom when Y is O, X is COR$_3$, and R$_1$ and R$_3$ are CH$_3$ are also useful for topical application to skin. The compositions comprise an effective amount, preferably from 0.001% to 10% of the dihydroxybenzoic acid derivative. The balance of the composition further comprises a pharmaceutically acceptable carrier. Suitable carriers for the dihydroxybenzoic acid derivatives remain in place on the skin as a continuous film and resist being washed off easily by perspiration or by immersion in water. Generally, the carrier is organic in nature and capable of having dispersed or dissolved therein the dihydroxybenzoic acid derivative. Lotions, creams, solutions, gels and solids are common physical forms of the compositions herein. More detailed description of such forms follows.

By "topical application" herein is meant directly laying on or spreading the compounds and compositions on epidermal tissue (including outer skin and oral, gingival, nasal, etc. tissue) at the afflicted situs on the epidermal tissue, or, on the epidermal tissue at or closest to the afflicted situs if an analgesic/anti-inflammatory action is sought for disorders of deeper structures.

Lotions

Lotions comprise from 0.001% to 10%, preferably 0.01% to 5% of the dihydroxybenzoic acid derivative, from 1% to 25%, preferably 3% to 15% of an emollient, and the balance water. Several emollients are known. Examples of classes of emollients and examples thereof follow.

1. Hydrocarbon oils and waxes. Examples thereof are mineral oil, petrolatum, paraffin, ceresin, ozokerite, microcrystalline wax, polyethylene, and perhydrosqualene.
2. Silicone oils, such as dimethyl polysiloxanes, methylphenyl polysiloxanes, water-soluble and alcohol-soluble silicone glycol copolymers.
3. Triglyceride esters, for example vegetable and animal fats and oils. Examples include castor oil, safflower oil, cottonseed oil, corn oil, olive oil, cod liver oil, almond oil, avocado oil, palm oil, sesame oil, and soybean oil.
4. Acetoglyceride esters, such as acetylated monoglycerides.
5. Ethoxylated glycerides, such as ethoxylated glyceryl monostearate.
6. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples thereof include oleyl myristate, oleyl stearate, and oleyl oleate.
8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.
9. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanol alcohols are examples of satisfactory fatty alcohols.
10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.
11. Ether-esters such as fatty acid esters of ethoxylated fatty alcohols.
12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.
13. Polyhydric alcohols and polyether derivatives. Propylene glycol, dipropylene glycol, polypropylene glycol 2000, 4000, polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol 200–6000, methoxy polyethylene glycols 350, 550, 750, 2000, 5000, poly-[ethylene oxide] homopolymers (100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol, and polyoxypropylene derivatives of trimethylolpropane are examples thereof.
14. Polyhydric alcohol esters. Ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
15. Wax esters such as beeswax, spermaceti, myristyl myristate, stearyl stearate.
16. Beeswax derivatives, e.g. polyoxyethylene sorbitol beeswax. These are reaction products of beeswax with ethoxylated sorbitol of varying ethylene oxide content, forming a mixture of ether-esters.
17. Vegetable waxes including carnauba and candelilla waxes.
18. Phospholipids such as lecithin and derivatives.
19. Sterols. Cholesterol, cholesterol fatty acid esters are examples thereof.
20. Amides such as fatty acid amides, ethoxylated fatty acid amides, solid fatty acid alkanolamides.

The lotions of this invention further comprise from 1% to 10%, preferably 2% to 5% of an emulsifier. Emulsifiers are of a nonionic, anionic or cationic class. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglyceride wherein the fatty acid moiety contains from 10 to 20 carbon atoms, diethylene glycol, polyethylene glycols of molecular weight 200 to 6000, propylene glycol of molecular weight 200 to 3000, glycerol, sorbitol, sorbitan, polyoxyethylene sorbitol, polyoxyethylene sorbitan, and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceeding paragraphs also have emulsifying properties. When a lotion is formulated containing such an emollient, an additional emulsifier is not needed, though it can be included in the composition.

The balance of the composition is water. The lotions are formulated by simply admixing all of the components together. Preferably the dihydroxybenzoic acid derivative is dissolved in the emollient and the mixture is added to the water. Optional components such as the emulsifier or common additives can be included. One common additive is a thickening agent at a level from 1% to 10% of the composition. Examples of suitable thickening agents include: cross-linked carboxy polymethylene polymers, methyl cellulose, polyethylene glycols, gum tragacanth, gum kharaya, xanthan gums and bentonite.

Creams

Compositions of this invention also can be formulated in a cream form. The creams comprise from 0.001% to 10%, preferably 0.01% to 5% of the dihydroxybenzoic acid derivative, from 5% to 50%, preferably 10% to 25% of an emollient, and the balance water. The emollients above described are also used in the cream form of the composition. Optionally the cream form contains a suitable emulsifier. Emulsifiers described above are useful herein. When an emulsifier is included, it is in the composition at a level from 3% to 50%, preferably 5% to 20%.

Solutions

The compositions of this invention can be also formulated in a solution form. The solution form of the composition comprises from 0.001% to 10%, preferably 0.01% to 5% of the dihydroxybenzoic acid derivative and the balance a suitable organic solvent. Suitable organic materials useful as the solvent or a part of a solvent system are as follows: propylene glycol, polyethylene glycol (200–600) polypropylene glycol (425–2025), glycerine, sorbitol esters, 1,2,6-hexanetriol, ethanol, isopropanol, diethyl tartrate, butanediol, and mixtures thereof. Such solvent systems can also contain water.

These compositions are applied to the skin in the solution form, or the solutions are formulated in an aerosol form and applied to the skin as a spray-on. The compositions in the aerosol form further comprise from 25% to 80%, preferably 30% to 50% of a suitable propellant. Examples of such propellants are: the chlorinated, fluorinated and chlorofluorinated lower molecular weight hydrocarbons. Nitrous oxide and carbon dioxide are also used as propellant gases. They are used at a level sufficient to expel the contents of the container.

Gels

Compositions herein are formulated into a gel form by simply admixing a suitable thickening agent to the above-described solution compositions. Examples of suitable thickening agents are described above with respect to the lotions.

The gelled compositions comprise from 0.001% to 10%, preferably 0.01% to 5% of the dihydroxybenzoic acid derivative; from 5% to 75%, preferably 10% to 50% of an organic solvent as above described; from 0.5% to 20%, preferably 1% to 10% of the thickening agent; and the balance water.

Solids

The compositions of this invention are also formulated into a solid form. Such forms have use as a stick-type composition intended for application to the lips or other parts of the body. Such compositions comprise from 0.001% to 10%, preferably 0.01% to 5% of the dihydroxybenzoic acid derivative and from 50% to 98%, preferably 60% to 90% of the above described emollient. This composition can further comprise from 1% to 20%, preferably from 5% to 15% of a suitable thickening agent, and optionally emulsifiers and water. Thickening agents as described above with respect to the gelled compositions are suitable herein.

Additives commonly found in topical compositions such as preservatives, e.g. methyl and ethyl-paraben, dyes and perfume can be included in any of the aforedescribed compositions.

Method of Application

The effective amount of the dihydroxybenzoic acid derivative used topically will vary with the particular circumstances of application, the duration of the anticipated exposure, and like considerations. Generally, the amount will range from 0.01 μg to 500 μg of the dihydroxybenzoic acid derivative per square centimeter of epidermal area. Single applications for treatment of inflammation of the skin preferably range from 0.01 μg to 50 μg of the dihydroxybenzoic acid derivative per square centimeter of epidermal area. Greater amounts are uneconomical and provide no noticeable increased activity while lesser amounts do not provide a noticeable beneficial effect. Single applications for treatment of inflammation of deeper structures, e.g. muscles, tendons, bursa and joints preferably range from 0.1 μg to 500 μg dihydroxybenzoic acid derivative per square centimeter of epidermal area. It is to be understood the amount of topical composition (dihydroxybenzoic acid derivative plus carrier) applied to the affected epidermal areas is easily determined based on the amount of dihydroxybenzoic acid derivative contained therein.

The following examples are illustrative of the compositions herein and their manner of use.

EXAMPLE XI

The compositions of this invention are evaluated for their anti-inflammation properties using a guinea pig ultraviolet light induced erythema test.

Hartley strain albino guinea pigs weighing between 400 and 500 grams are clipped on the dorsal area and then depilated using a cream hair remover. 15 minutes after the application of the hair remover, the area is thoroughly washed using warm tap water and then dried with a towel. After a period of about 18 hours, the guinea pigs are irradiated in a wire cage for 30 minutes using a bank of four FS 40 Westinghouse lights at a distance of 31 cm. Ten minutes irradiation constitutes a minimal erythema dose. An adhesive tape strip is attached to the center of the guinea pig's back to retain an unirradiated portion of skin. About 1 hour after irradiation time, 3 preparations are applied on each side using a micropipette. The treated areas are about 1×4 cm in size and are aligned vertically from near the center back down the side. The degree of blanching is determined at hourly intervals.

Compositions as below are formulated and tested.

| | |
|---|---|
| Propylene glycol | 49.95% |
| Ethanol | 49.95% |
| *Dihydroxybenzoic acid derivative | 0.1% |

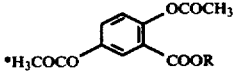

Comparisons of the anti-inflammatory activity of the dihydroxybenzoic acid derivatives are made by calculating their $IC_{50}$ values. That is, compounds commonly show a dose-response relationship such that higher concentrations produce a greater response and lower concentrations a lower response. However, different compounds have steeper or flatter slopes of their dose-response curves so that comparison of activity at one or a few concentrations does not give a realistic understanding of their relative activities. In order to better relate the activity of several compounds by a single number, the concentration of compound which inhibits a function by 50% is calculated from the dose-response curve. This term is called the $IC_{50}$, (the concentration which inhibits the function by 50%). In the following table the $IC_{50}$ refers to concentrations (expressed in millimoles) of the dihydroxybenzoic acid derivative which inhibits UV-induced erythema by 50%. These $IC_{50}$ data are based on cumulative blanching grades over a 1–4 hour period after application of the dihydroxybenzoic acid derivative. The lower the $IC_{50}$ value, the greater is the compound's activity.

| R | $IC_{50}$ |
|---|---|
| $CH_2C_6H_5$ | 0.4 |
| $CH_3$ | 2.3 |
| $C_2H_5$ | 1.8 |
| $C_3H_7$ | 1.1 |
| $C_4H_9$ | 1.2 |

-continued

| R | IC$_{50}$ |
|---|---|
| C$_6$H$_{13}$ | 0.34 |
| C$_8$H$_{17}$ | 0.34 |
| C$_{10}$H$_{21}$ | 0.65 |
| C$_{12}$H$_{25}$ | 1.2 |
| C$_2$H$_3$(C$_2$H$_5$)C$_4$H$_9$ | 5.8 |
| CH(C$_6$H$_5$)CH$_3$ | 1.2 |
| CH$_2$C$_6$H$_4$OCH$_3$ | 0.53 |
| CH$_2$C$_6$H$_3$(OCH$_3$)$_2$ | 5.0 |
| CH$_2$C$_6$H$_4$CH$_3$ | 0.53 |
| CH$_2$C$_6$H$_4$F | 0.60 |

When aspirin is used in place of the dihydroxybenzoic acid derivative an IC$_{50}$ value of 140 millimoles is obtained. The above results show the compounds of this invention possess anti-inflammation properties significantly better than aspirin when applied topically.

EXAMPLE XII

Clinical Evaluation of the Safety and Efficacy of Topical Preparations in Humans in an Ultraviolet Light-induced Erythema and/or Pain Test The UV-induced erythema and/or pain model consists of creating a burn with ultraviolet light (UV) and treating the resultant erythemal reaction with topical applications of the new drug formulations. At various time intervals, the degree of erythema and the pain tolerance response to radiant heat are monitored.

The model is useful in demonstrating optimal conditions for delivery of the drug to the site of action. Experiments have been designed to determine the effectiveness of benzyl 2,5-diacetoxybenzoate according to several parameters: treatment times, concentration of drug, repeated applications, duration of response, and vehicles.

Among the criteria for subject admission into this study were:
1. Each subject would be a normal, healthy Caucasian male volunteer.
2. None of the subjects would be hypersensitive to sunlight.
3. None of the subjects would use any type of drug therapy which might exaggerate the effects of the UV-irradiation, or interfere with and/or enhance the action of the drug.
4. No subject would be used more than 4 times during the course of the study at intervals of at least one week.

A total of 56 subjects were actually used in the UV-induced erythema and pain tests.

The compositions of the test formulations employed in these studies were as follows:
(A)* 0.01–1.0% (w/w) benzyl 2,5-diacetoxybenzoate in propylene glycol/ethanol (50/50, w/w);
(B)* 0.01–2.0% (w/w) benzyl 2,5-diacetoxybenzoate in ethanol/water (80/20, w/w);
(C) Propylene glycol/ethanol (50/50, w/w);
(D) Ethanol/water (80/20, w/w);
(E) 0.01–0.5% (w/w) benzyl 2,5-diacetoxybenzoate in ethanol/propylene glycol/water (50/10/40, w/w/w);
(F) Ethanol/propylene glycol/water (50/10/40, w/w/w);
(G)* 0.025 to 2.5% (w/w) benzyl 2,5-diacetoxybenzoate in a cream vehicle;
(H) Placebo cream vehicle;

*The UV-induced erythema tests were designed to evaluate a range of concentrations of the drug substance.

Induction of Erythema: Subjects were irradiated on a 2.5×20 cm area on their backs, using a bank of three 20S Westinghouse fluorescent lamps at a distance of 15 cm. Each subject received 2 to 4 MEDs of light (minimum erythemal dose) for these experiments.

Treatment with Formulations: The UV-irradiated area was divided into 4 treatment sites. When liquid formulations were tested, up to 40 microliter were topically applied to each treatment site using an Eppendorf micropipet. When cream formulations were tested, no more than 100 microliter were topically applied to each treatment site using a 1 cc tuberculin syringe with no needle; the cream was rubbed into the skin with a gloved finger.

Each site was treated no more than 4 times, and all treatments occurred within the 24-hour interval following UV-irradiation.

A randomixed treatment sequence was used.

The table below gives a general outline of the tests used to measure the safety and efficacy of the benzyl 2,5-diacetoxybenzoate:

| | Measure | Frequency of Measure | Units of Measure |
|---|---|---|---|
| | | | Grader's Evaluation |
| 1. | Anti-erythemic Activity | At suitable time intervals within 31 hours after UV-irradiation. | 0 to 4 scale, 0 = no blanching 4 = complete blanching to color of non-irradiated, non-treated adjacent skin |
| 2. | Analgesic Activity | At suitable time intervals within 31 hours after UV-irradiation. | Elapsed time, in seconds, to respond to a radiant heat pain stimulus on treated and untreated skin. |

A summary of the conclusions derived from these studies is presented below.

1. ANTI-ERYTHEMIC ACTIVITY (BLANCHING)

a. Treatment Time

Application of the new drug formulations varied from a few minutes to 24 hours following UV-irradiation. In general, the earlier a given treatment was made after UV-irradiation, the greater the blanching response.

b. Concentration

Concentrations from 0.01 to 2.5% benzyl 2,5-diacetoxybenzoate were tested. In the first 3–4 hours after a single application, 0.03–2.5% benzyl 2,5-diacetoxybenzoate caused very similar responses; however, the blanching response with 0.01% benzyl 2,5-diacetoxybenzoate was distinctly weaker. This suggests that there is saturation either in the rate of penetration or at the site of action by concentrations of the compound as low as 0.03%. The higher concentrations of benzyl 2,5-diacetoxybenzoate maintained some degree of blanching for 5–11 hours after treatment in a dose-related manner.

c. Repeated Application

Application of the test formulations varied from 1 to 4 times within a 24-hour period. Repeated application of formulations containing low concentrations of benzyl 2,5-diacetoxybenzote, e.g., 0.03% caused a high blanching response. Alternatively, multiple application of higher levels of the compound (1 to 2.5%) did not produce an effect greater than obtained with a single application.

d. Duration of Response

Evaluation of the blanching response from 1 to 24 hours following treatment indicated that the maximum response was usually 2–3 hours after drug treatment. The half-life of the response (the time for the maximum response to diminish 50%) was about 9 hours after drug treatment.

e. Vehicles

When the peak blanching responses at a given concentration of benzyl 2,5-diacetoxybenzoate in various vehicle systems were compared, the effectiveness of the vehicles were ranked as follows in decreasing order of effectiveness:
 propylene glycol/ethanol (50/50, w/w)
 ethanol/propylene glycol/water (50/10/40, w/w/w) = cream
 ethanol/water (80/20, w/w)

We conclude that benzyl 2,5-diacetoxybenzoate has anti-erythemic activity in this inflammatory reaction which has been shown to be associated with a prostaglandin-mediated phase.

2. ANALGESIC ACTIVITY

Skin irradiated with 3–4 MEDs (minimal erythemal doses) of UV-B light (normal sunburn range) becomes hyperalgesic to radiant heat in about four hours. Treatment of irradiated subjects with benzyl 2,5-diacetoxybenzoate demonstrated analgesic activity in the following manner:

a.

Analgesic activity was demonstrated in skin which was treated 2 to 6 hours following UV-irradiation. Statistically significant analgesia was found in 9 out of 12 tests where the vehicle for the new compound substance was propylene glycol/ethanol (50/50, w/w). In 8 out of the 12 tests, at least one concentration of benzyl 2,5-diacetoxybenzoate at one time point effected at least an 80% return to normal pain tolerance.

b. Concentration

The analgesic response is dose-dependent:

| % Benzyl 2,5-diacetoxybenzoate in Propylene Glycol/Ethanol (50/50, w/w) | Tests with Analgesic Responses | Pain Tolerance | |
|---|---|---|---|
| | | No. of Subjects | Time Seconds + SE[b] |
| 1.0 | 9/12 | 44 | $2.2^2 \pm 0.6$ |
| 0.1 | 2/6 | 16 | $1.4^2 \pm 0.6$ |
| 0.01 | 1/6 | 13 | $0.7^2 \pm 0.4$ |
| (Normal skin minus nontreated skin) | — | 37 | $4.0 \pm 0.5$ |

[a]UV-irradiated treated skin (−) UV-irradiated nontreated skin
[b]Standard error between tests c. Repeated Applications

A few tests were conducted to determine the effects of multiple applications on analgesic activity. At 1% benzyl 2,5-diacetoxybenzoate, repeated application failed to increase the level of analgesic activity effected by a single application. However, three applications of 0.25% benzyl, 2,5-diacetoxybenzoate were more effective than 2 or 1 applications.

d. Duration of Response

Treatments with 1% (w/w) benzyl 2,5-diacetoxybenzoate in propylene glycol/ethanol (50/50, w/w) were made 2 to 6 hours after UV-irradiation. Maximum analgesic activity was observed in the 2–4 hour interval following treatment. Some analgesic effects from the formulation were observed up to 10 hours after treatment(s).

| Hours after Treatment | No. of Subjects | Recovery of Treated Skin[a] | |
|---|---|---|---|
| | | Sec. | + SE[a] |
| 2–4 | 22 | 2.4 | 0.5 |
| 5–7 | 16 | 1.6 | 0.4 |
| 8–10 | 6 | 1.4 | 0.7 |
| (Normal skin minus non-treated skin) | 37 | 4.0 | 0.5 |

[a]As compared to normal skin and nontreated UV-irradiated skin
[b]Standard error between tests e. Vehicles

Comparison of analgesic responses obtained from treatment with benzyl 2,5-diacetoxybenzoate in 4 vehicle systems indicated that the propylene glycol/ethanol (50/50, w/w) vehicle delivered the strongest analgesic activity. This vehicle also provided the highest antierythemic activity.

Ethanol/water (80/20, w/w), ethanol/propylene glycol/water (50/10/40, w/w/w), and a cream formulation were all somewhat less effective than propylene glycol/ethanol in delivering an efficacious dose of benzyl 2,5-diacetoxybenzoate into the skin.

f. Non-irradiated Skin

In some tests, non-irradiated skin was also treated with the new compound. No evidence of analgesic action was found. Thus, only skin which was hyperalgesic following UV irradiation demonstrated analgesic effects of the drug. We conclude that benzyl 2,5-diacetoxybenzoate does have topical analgesic activity for rather severe and acute pain.

IV. Statistical Analysis

The experimental design was regarded as randomized blocks, in which the subject is the "block". The variation between subjects with respect to erythema or analgesic response was accounted for as a source of variation in the Analysis of Variance (ANOVA). When ANOVA indicated that significant treatment effects existed, the Least Significant Difference (LSD) was used to determine the active from control treatment.

Discussion of this type of statistical analysis is found in *Statistical Methods*, G. W. Snedecor and W. G. Cochran, 6th Edition, Iowa State University Press, Ames, Iowa (1967).

EXAMPLE XIII

This example illustrates the efficacy of the dihydroxybenzoic acid derivatives described herein for suppressing the inflammation associated with arthritis.

Male Sprague-Dawley rats, weighing between 180–200 grams, are injected subcutaneously in the distal third of the tail with a suspension of 0.8 mg of heat-killed Mycobacterium butyricum in 0.1 ml of mineral oil. This injection introduces arthritis into the rat as evidenced by pedal edema (swelling). Measurement of the alleviation of the inflammation associated with the arthritis is made by determining the volume of the hind paws initially, two weeks later, and each subsequent week thereafter. The paw volume measurements are obtained by immersing each rat's hind paw up to a predetermined mark in a mercury bath connected to a Statham pressure transducer. The increase in pressure within the bath is proportional to the volume of the paw introduced.

A solution of benzyl 2,5-diacetoxybenzoate is made. The solution comprises a 1:1 mixture of propylene glycol and ethanol and 2% benzyl 2,5-diacetoxybenzoate. In one group, each rat is treated topically with 20 mg/kg/day of the benzyl 2,5-diacetoxybenzoate solution. The changes in paw volume after each treatment are compared to the control rats. At the end of five weeks of treatment, the rats treated with the benzyl 2,5-diacetoxybenzoate show significant improvement compared to the non-treated control group as evidenced by a reduction in pedal edema. The reduction in pedal edema is comparable to that obtained in a control group which had been administered 200 mg/kg/day of aspirin by an oral route (i.e. 10 times the dosage of the topically applied benzyl 2,5-diacetoxybenzoate).

The compositions in the following example are exemplary of various composition forms.

EXAMPLE XIV

| Lotion | |
|---|---|
| Isopropyl myristate | 8% |
| Corn oil | 5% |
| Propylene glycol | 5% |
| Triethanolamine oleate | 5% |
| Benzyl 2,5-diacetoxybenzoate | 0.25% |
| Xanthan gum | 0.5% |
| Water | Balance |
| Cream | |
| Isopropyl myristate | 3% |
| Sorbitol | 5% |
| Propylene glycol | 10% |
| Triethanolamine stearate | 17% |
| Hexyl 2,5-diacetoxybenzoate | 1% |
| Water | Balance |
| Gel | |
| Oleyl alcohol | 1% |
| Propylene glycol | 19% |
| Ethyl 2,5-dipropionoxybenzoate | 2% |
| Triethanolamine | 0.5% |
| Ethanol | 57% |
| Carbopol 940* | 0.5% |
| Water | Balance |
| Solution | |
| Propylene glycol | 10% |
| Polyethylene glycol 400 | 2% |
| Benzyl 2,5-diacetoxybenzoate | 0.5% |
| Ethanol | 48% |

| -continued | |
|---|---|
| Water | Balance |
| Ointment | |
| Oleyl alcohol | 30% |
| Cetyl alcohol | 40% |
| Propylene glycol | 26% |
| Phenyl 2,5-diacetoxybenzoate | 4% |

*Carbopol 940 is a carboxy vinyl polymer available from the B.F. Goodrich Chemical Co.

The compositions of Example XIV are topically applied to relieve the inflammation and skin irritation of acne and acneiform skin diseases.

Oral and Other Compositions

The 2,5-dihydroxybenzoic acid derivatives disclosed above are also useful when used systemically, for example by oral or parenteral administration. The required dosage of 2,5-dihydroxybenzoic acid derivatives to be both safe and effective will vary with the particular condition being treated, the severity of the condition, the duration of treatment, the specific derivative employed and its usage concentration, and like factors within the specific knowledge and expertise of the patient or the attending physician and commensurate with a reasonable benefit/risk ratio associated with the use of any drug compound. The systemic dosages and dosage ranges given herein are based on delivery of the 2,5-dihydroxybenzoic acid derivatives to a 70 kg human and can be adjusted to provide equivalent dosages for patients of different body weights. Oral dosages can range from about 0.05 g to about 50 g per day, usually and preferably in divided doses. Preferably, dosages ranging from about 0.1 g to about 20 g per day, most preferably from about 0.25 g to about 10 g per day, are employed when the 2,5-dihydroxybenzoic acid derivatives are administered orally.

The 2,5-dihydroxybenzoic acid derivatives can also be administered parenterally in combination with a pharmaceutically acceptable carrier such as sterile, pyrogen-free water at from about 0.5 mg to about 200 mg of 2,5-dihydroxybenzoic acid derivative per dose. Parenteral administration of from 0.5 mg to 200 mg per day can be by subcutaneous, intradermal, intramuscular, intraarticular, or intravenous injection. The preferred dosage range by these modes of administration is usually in the range of from about 1 to about 100 mg per day.

For oral administration the 2,5-dihydroxybenzoic acid derivatives can be formulated in unit dosage forms such as pills, capsules, tablets, granules, solutions, elixirs, troches, chewing gum, chewable tablets, and the like. Suppositories containing the compounds herein can be formulated in well known fashion. The oral unit dosage forms typically include the dihydroxybenzoic acid derivative and a pharmaceutical carrier, each unit dosage form containing from about 15 mg to about 1 g of derivative. The preferred quantity of derivative in unit dosage forms intended for oral use by humans ranges from 25 mg to 750 mg, more preferably from 100 mg to 500 mg.

As used herein the term "pharmaceutically acceptable carrier" denotes a solid or liquid filler, diluent, or encapsulating substance. Some examples of the substances which can serve as pharmaceutical carriers to 2,5-dihydroxybenzoic acid derivatives include: sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc, stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; phosphate buffer solutions; cocoa butter (suppository base), as well as other non-toxic compatible substances typically used in pharmaceutical formulations. Wetting agents and lubricants such as sodium lauryl sulfate, as well as coloring agents, flavoring agents and preservatives, can also be present. Well-known enteric coating agents can be used with such oral products so that the 2,5-dihydroxybenzoic acid derivative is spared the acidic environment of the stomach and can be absorbed through the walls of the intestines.

The pharmaceutical carrier employed in conjunction with the dihydroxybenzoic acid derivatives is used at a concentration sufficient to provide a practical size to dosage relationship. Preferably, the pharmaceutical carrier comprises from about 0.1% to about 99% by weight of the total composition.

The following examples are illustrative of the compositions for oral or parenteral use herein and their manner of use.

EXAMPLE XV

Capsules are prepared by conventional methods comprised as follows:
Benzyl 2,5-diacetoxybenzoate: 300 mg/capsule
Starch: 75 mg/capsule
Sodium lauryl sulfate: 2.9 mg/capsule The above capsules administered orally, two capsules every six hours to a 70 kg patient, substantially reduce inflammation and provide an analgesic effect to treat common ailments such as simple headache, arthritis, rheumatism, gout, bursitis, backache, sciatica, toothache, and sore throat.

EXAMPLE XVI

Tablets are prepared by conventional methods, formulated as follows:
p-Acetamidophenyl 2,5-diacetoxybenzoate: 60 mg/tablet
Lactose: 40 mg/tablet
Starch: 2.50 mg/tablet
Sodium carboxymethylcellulose: 1.00 mg/tablet When administered at the rate of two tablets every four hours, the above composition significantly reduces the pain of minor skin inflammation by providing an analgesic effect.

The lactose employed in this example is replaced by sucrose and the sodium carboxymethylcellulose by magnesium stearate without affecting the properties of the tablet.

Tablets prepared by conventional methods are effective in providing an analgesic or anti-inflammatory effect when the 2,5-diacetoxybenzoate of the above formulation is replaced by other derivatives of 2,5-dihydroxybenzoic acids. For example:
6'-Methylamidohexyl 2,5-diacetoxybenzoate
2'-Ethyl-2',4'-hexadienyl2,5-diacetoxybenzoate
2'-Acetoxybenzyl 2,5-dipropionoxybenzoate
2'-Fluorobenzyl 2,5-diacetoxybenzoate
2'-Hydroxybenzyl 2,5-diacetoxybenzoate
2'-Methoxybenzyl 2,5-diacetoxybenzoate
2',4'-Diacetoxybenzyl 2,5-diacetoxybenzoate
2'-Acetamidobenzyl 2,5-diacetoxybenzoate
Isopropyl 2,5-diacetoxybenzoate
Propyl 2,5-diacetoxybenzoate
2'-ethylhexyl 2,5-diacetoxybenzoate
Decyl 2,5-diacetoxybenzoate
Dodecyl 2,5-diacetoxybenzoate
Methyl 2,5-dipropionoxybenzoate
Octyl 2,5-dipropionoxybenzoate
Hexyl 2,5-dipivaloxybenzoate
Decyl 2,5-dibutyroxybenzoate
Butyl 2-acetoxy-5-hydroxybenzoate
Hexyl 2-propionoxy-5-hydroxybenzoate
3',5'-Hexadienyl 2,5-diacetoxybenzoate
2'-Hexenyl 2,5-diacetoxybenzoate
9',11'-Dodecadienyl 2,5-diacetoxybenzoate
Benzyl 2,5-dibutyroxybenzoate
Benzyl 2,5-diacetoxybenzoate
Benzyl 2,5-dipivaloxybenzoate
Benzyl 2-acetoxy-5-hydroxybenzoate
Phenyl 2,5-diacetoxybenzoate
Phenyl 2-acetoxy-5-hydroxybenzoate
2,5-Diacetoxy-N-hexylbenzamide
2,5-Dipropionoxy-N-octylbenzamide
2,5-Diacetoxy-N-dibutylbenzamide
Hexyl 2,5-diacetoxybenzoate
5'-Hydroxyhexyl 2,5-diacetoxybenzoate
6'-Acetoxyhexyl 2,5-diacetoxybenzoate
6'-Fluorohexyl 2,5-diacetoxybenzoate and
6'-Nitrohexyl 2,5-diacetoxybenzoate

EXAMPLE XVII

Elixirs of dihydroxybenzoic acid derivatives for infants over one year of age are prepared by conventional means with formulations as follows:
Benzyl 2,5-diacetoxybenzoate: 150 mg
Compound tragacanth powder: 100 mg
Raspberry syrup: 1 ml
Propylene glycol (1,2-propanediol): 10 ml Ten mls of the foregoing composition are administered orally to alleviate toothache.

EXAMPLE XVIII

Dihydroxybenzoic acid derivatives are formulated for administration by injection. The injection mixtures are prepared by conventional means immediately before administration and are formulated as follows for a single dose.
Benzyl 2,5-diacetoxybenzoate: 10 mg
NaCl: 90 mg
Water to bring total volume to 10 ml; pH 6 to 6.5; sterilized Parenteral formulations of the above compositions are administered i.v. to provide an analgesic or antiinflammatory effect in patients suffering discomfort such as postoperative pain or having discomfort under circumstances when oral administration is inappropriate or contraindicated.

As can be seen from the foregoing, the topical and oral compositions herein comprise a safe and effective amount of a 2,5-dihydroxybenzoic acid derivative and are effective when used both systemically and topically. By the term "comprise" as used herein is meant that various other inert ingredients, compatible drugs and medicaments, and steps can be conjointly employed in the compositions and processes of this invention as long as the critical 2,5-dihydroxybenzoic acid derivatives are present in the compositions and are used in the manner disclosed. The term "comprising" thus encompasses and includes the more restrictive terms "consisting essentially of" and "consisting of" which characterize the use of the essential 2,5-dihydroxybenzoic acid derivatives in the compositions and methods disclosed herein.

By "compatible" herein is meant that the components of the compositions are capable of being co-mingled without interacting in a manner which would substantially decrease the efficacy of the total compositions under ordinary use situations.

It is also seen from the foregoing that this invention encompasses methods for providing an analgesic effect and alleviating inflammation comprising topically applying or systemically administering a safe and effective amount, usually from about 0.01 mg to about 50 g per patient per day, of a 2,5-dihydroxybenzoic acid derivative, usually with a pharmaceutically acceptable carrier. The methods, compositions, and derivatives are used to treat acne and acneiform skin diseases and to provide an analgesic effect and alleviate inflammation in various disorders at the deeper structures, muscles, tendons, bursa and joints associated with disease and trauma, and in various other conditions in which salicylate compounds such as aspirin have heretofore been used to alleviate pain and discomfort.

The compositions herein are much more effective antiinflammatory/analgesics than aspirin when applied topically. When administered systemically, the compositions herein are at least as effective as aspirin, yet have much lower toxicity than aspirin and do not exhibit the negative side-effects (stomach bleeding, etc.) associated with aspirin.

What is claimed is:

1. A compound of the formula

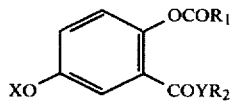

wherein $R_1$ is an alkyl group having from 1 to 4 carbon atoms, Y is O, $R_2$ is an alkyl group having from 6 to 8 carbon atoms or benzyl and X is $COR_3$ where $R_3$ is an alkyl group having from 1 to 4 carbon atoms.

2. The compound of claim 1 wherein $R_2$ is benzyl.

3. The compound of claim 1 wherein $R_2$ is an alkyl group having from 6 to 8 carbon atoms.

4. The compound of claim 3 wherein $R_2$ is a hexyl group.

5. The compound of claim 1 wherein $R_1$ and $R_3$ are tertiary butyl groups.

6. The compound of claim 1 wherein $R_1$ and $R_3$ are methyl groups.

7. Benzyl 2,5-diacetoxybenzoate.

8. Hexyl 2,5-diacetoxybenzoate.

9. A composition to provide an analgesic effect and alleviate inflammation comprising:

(a) an effective amount of a 2,5-dihydroxybenzoic acid derivative of the formula

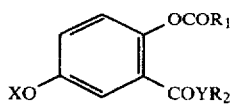

wherein $R_1$ is an alkyl group having from 1 to 4 carbon atoms; Y is O, $R_2$ is an alkyl group having from 6 to 8 carbon atoms or benzyl and X is $COR_3$ wherein $R_3$ is an alkyl group having from 1 to 4 carbon atoms; and (b) the balance a pharmaceutically acceptable carrier.

10. The composition of claim 9 wherein $R_2$ is benzyl.

11. The composition of claim 9 wherein $R_2$ is an alkyl group having from 6 to 8 carbon atoms.

12. The composition of claim 11 wherein $R_2$ is a hexyl group.

13. The composition of claim 9 wherein $R_1$ and $R_3$ are tertiary butyl groups.

14. The composition of claim 9 wherein $R_1$ and $R_3$ are methyl groups.

15. The composition of claim 9 wherein the dihydroxybenzoic acid derivative is benzyl 2,5-diacetoxybenzoate.

16. The composition of claim 9 wherein the dihydroxybenzoic acid derivative is hexyl 2,5-diacetoxybenzoate.

17. The composition of claim 9 for topical application to skin wherein the dihydroxybenzoic acid derivative represents from 0.001% to 10% of the composition.

18. The composition of claim 17 in the form of a lotion comprising:

(a) the dihydroxybenzoic acid derivative;

(b) from 1% to 25% of an emollient; and (c) the balance water.

19. The composition of claim 18 further comprising from 1% to 10% of an emulsifier.

20. The composition of claim 17 in the form of a cream comprising:

(a) the dihydroxybenzoic acid derivative;

(b) from 5% to 50% of an emollient; and (c) the balance water.

21. The composition of claim 20 further comprising from 3% to 50% of an emulsifier.

22. The composition of claim 17 in the form of a solution comprising:

(a) the dihydroxybenzoic acid derivative; and (b) the balance an organic solvent.

23. The composition of claim 17 in the form of a gel comprising:

(a) the dihydroxybenzoic acid derivative;

(b) from 5% to 75% of an organic solvent;

(c) from 0.5% to 20% of a thickening agent; and (d) the balance water.

24. The composition of claim 17 in the form of a solid comprising:

(a) the dihydroxybenzoic acid derivative; and (b) from 50% to 98% of an emollient.

25. The composition of claim 9 for oral administration in unit dosage form comprising from about 15 mg to about 1 g of dihydroxybenzoic acid derivative and a pharmaceutically acceptable carrier.

26. The composition of claim 9 for parenteral administration comprising from about 0.5 mg to about 200 mg of dihydroxybenzoic acid derivative and a pharmaceutically acceptable carrier.

27. A method for topically providing an analgesic effect and alleviating inflammation comprising applying to the epidermal area so affected an effective amount of a dihydroxybenzoic acid derivative of the formula

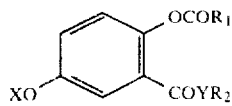

wherein $R_1$ is an alkyl group having from 1 to 4 carbon atoms, Y is O, $R_2$ is an alkyl group having from 6 to 8 carbon atoms or benzyl and X is $COR_3$ wherein $R_3$ is an alkyl group having from 1 to 4 carbon atoms.

28. The method of claim 27 wherein from 0.01 μg to 500 μg of the dihydroxybenzoic acid derivative is applied per square centimeter of epidermal area.

29. The method of claim 28 wherein the dihydroxybenzoic acid derivative is benzyl 2,5-diacetoxybenzoate.

30. The method of claim 28 wherein the dihydroxybenzoic acid derivative is hexyl 2,5-diacetoxybenzoate.

31. The method of claim 27 wherein the dihydroxybenzoic acid derivative is applied to the skin in the presence of a pharmaceutically acceptable carrier.

32. The method of claim 31 wherein inflammation of skin is treated with from 0.01 μg to 50 μg of the dihydroxybenzoic acid derivative per square centimeter of epidermal area.

33. The method of claim 31 wherein inflammation of muscles, tendons, bursa or joints is treated with from 0.1 μg to 500 μg of the dihydroxybenzoic acid derivative per square centimeter of epidermal area.

34. A method for providing an analgesic effect and alleviating inflammation comprising systemically administering to the affected person a safe and effective amount of a dihydroxybenzoic acid derivative of the formula

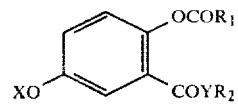

wherein $R_1$ is an alkyl group having from 1 to 4 carbon atoms, Y is O, $R_2$ is an alkyl group having from 6 to 8 carbon atoms or benzyl and X is $COR_3$ wherein $R_3$ is an alkyl group having from 1 to 4 carbon atoms.

35. The method of claim 34 wherein from about 0.05 g to about 50 g per day of the dihydroxybenzoic acid derivative is administered orally.

36. The method of claim 35 wherein the dihydroxybenzoic acid derivative is benzyl 2,5-diacetoxybenzoate.

37. The method of claim 35 wherein the dihydroxybenzoic acid derivative is hexyl 2,5-diacetoxybenzoate.

38. The method of claim 34 wherein from about 0.5 mg to about 200 mg per day of the dihydroxybenzoic acid derivative is administered parenterally.

39. The method of claim 38 wherein the 2,5-dihydroxybenzoic acid derivative is benzyl 2,5-diacetoxybenzoate.

* * * * *